(12) United States Patent
Weiman

(10) Patent No.: US 8,353,826 B2
(45) Date of Patent: Jan. 15, 2013

(54) TISSUE RETRACTOR AND METHOD OF USE

(75) Inventor: Mark Weiman, Coatesville, PA (US)

(73) Assignee: Globus Medical, Inc., Audubon, PA (US)

( * ) Notice: Subject to any disclaimer, the term of this patent is extended or adjusted under 35 U.S.C. 154(b) by 281 days.

(21) Appl. No.: 12/722,100

(22) Filed: Mar. 11, 2010

(65) Prior Publication Data

US 2011/0224496 A1    Sep. 15, 2011

(51) Int. Cl.
*A61B 1/32* (2006.01)

(52) U.S. Cl. ........................... 600/219; 600/231

(58) Field of Classification Search ........... 600/201–246
See application file for complete search history.

(56) References Cited

U.S. PATENT DOCUMENTS

| | | | |
|---|---|---|---|
| 5,067,477 A | 11/1991 | Santangelo | |
| 5,795,291 A | 8/1998 | Koros et al. | |
| 5,928,139 A | 7/1999 | Koros et al. | |
| 5,931,777 A | 8/1999 | Sava | |
| 5,944,658 A * | 8/1999 | Koros et al. | 600/232 |
| 6,074,343 A * | 6/2000 | Nathanson et al. | 600/214 |
| 6,083,154 A | 7/2000 | Liu et al. | |
| 6,322,500 B1 * | 11/2001 | Sikora et al. | 600/219 |
| 6,416,470 B2 | 7/2002 | Paolitto et al. | |
| 6,464,634 B1 | 10/2002 | Fraser | |
| 6,712,795 B1 | 3/2004 | Cohen | |
| 6,869,398 B2 * | 3/2005 | Obenchain et al. | 600/224 |
| 7,195,592 B2 | 3/2007 | Ravikumat et al. | |
| 7,344,495 B2 | 3/2008 | Ravikumar et al. | |
| 7,537,565 B2 | 5/2009 | Bass | |
| 7,556,600 B2 | 7/2009 | Landry et al. | |
| 7,618,367 B2 * | 11/2009 | Martin et al. | 600/224 |
| 7,850,608 B2 | 12/2010 | Hamada | |
| 7,976,463 B2 * | 7/2011 | Dewey et al. | 600/210 |
| 2005/0215863 A1 * | 9/2005 | Ravikumar et al. | 600/204 |
| 2006/0074278 A1 | 4/2006 | Petit et al. | |
| 2006/0224044 A1 | 10/2006 | Marchek et al. | |
| 2007/0021656 A1 | 1/2007 | Martin et al. | |
| 2007/0038033 A1 | 2/2007 | Jones et al. | |
| 2007/0073111 A1 * | 3/2007 | Bass | 600/215 |
| 2007/0073112 A1 | 3/2007 | Holmes | |
| 2007/0100212 A1 | 5/2007 | Pimenta et al. | |
| 2007/0123753 A1 | 5/2007 | Abdelgany | |
| 2007/0156025 A1 | 7/2007 | Marchek et al. | |
| 2007/0156026 A1 | 7/2007 | Frasier et al. | |
| 2007/0208228 A1 | 9/2007 | Pavento et al. | |
| 2007/0238932 A1 | 10/2007 | Jones et al. | |

(Continued)

FOREIGN PATENT DOCUMENTS

EP    1829488 A1    9/2007

OTHER PUBLICATIONS

International Search Report and Written Opinion in related matter PCT/US12/29539 mailed Jul. 13, 2012.

*Primary Examiner* — Kevin T. Truong
*Assistant Examiner* — Christopher Beccia

(57) ABSTRACT

Methods and devices for retracting tissue in a surgical procedure to allow access to the surgical site. Retractor systems and methods that comprise a retractor frame comprising rotatable arms and a linearly translatable arm, the rotatable arms and the linearly translatable arm each coupled to blades that can angulate.

20 Claims, 7 Drawing Sheets

U.S. PATENT DOCUMENTS

| | | |
|---|---|---|
| 2007/0282171 A1 | 12/2007 | Karpowicz et al. |
| 2008/0114208 A1* | 5/2008 | Hutton et al. .................. 600/201 |
| 2008/0114209 A1 | 5/2008 | Cohen et al. |
| 2008/0188718 A1 | 8/2008 | Spitler et al. |
| 2008/0249372 A1* | 10/2008 | Reglos et al. .................. 600/205 |
| 2009/0018401 A1 | 1/2009 | Kim |
| 2009/0069635 A1* | 3/2009 | Gephart et al. ............... 600/224 |
| 2009/0076516 A1 | 3/2009 | Lowry et al. |
| 2009/0124861 A1 | 5/2009 | Fetzer |
| 2009/0203969 A1* | 8/2009 | Cohen et al. .................. 600/245 |
| 2009/0227845 A1 | 9/2009 | Lo et al. |
| 2010/0113885 A1 | 5/2010 | McBride et al. |
| 2010/0152603 A1 | 6/2010 | Miles et al. |

* cited by examiner

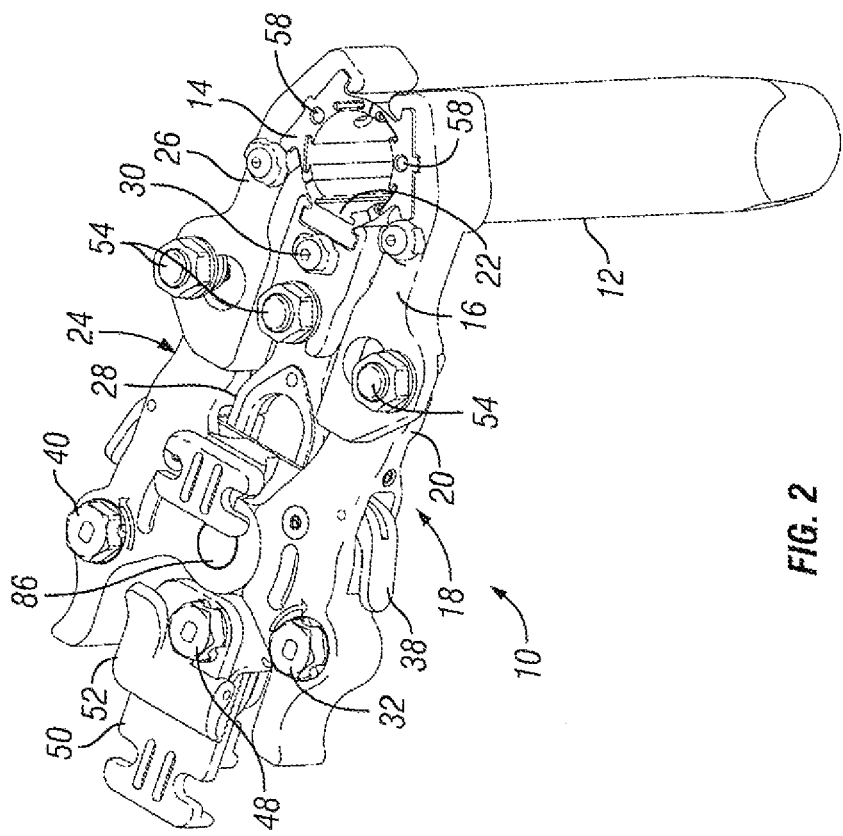
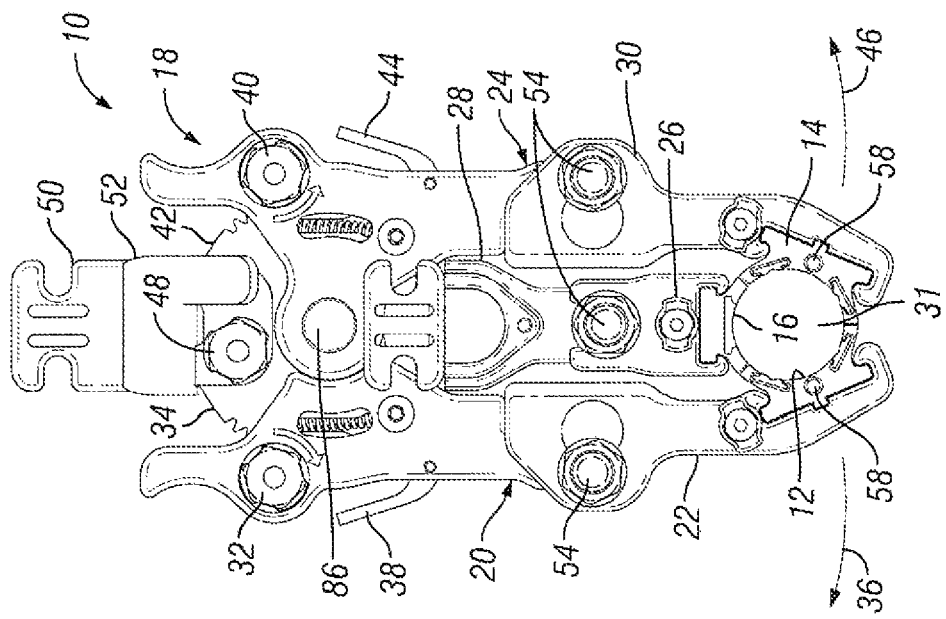
FIG. 1
FIG. 2

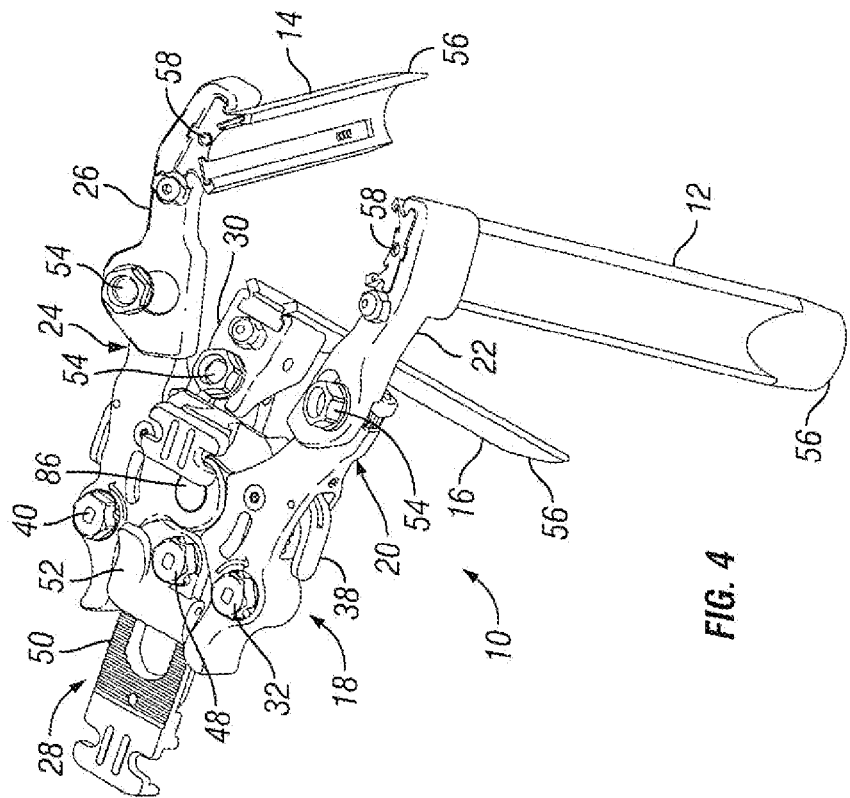
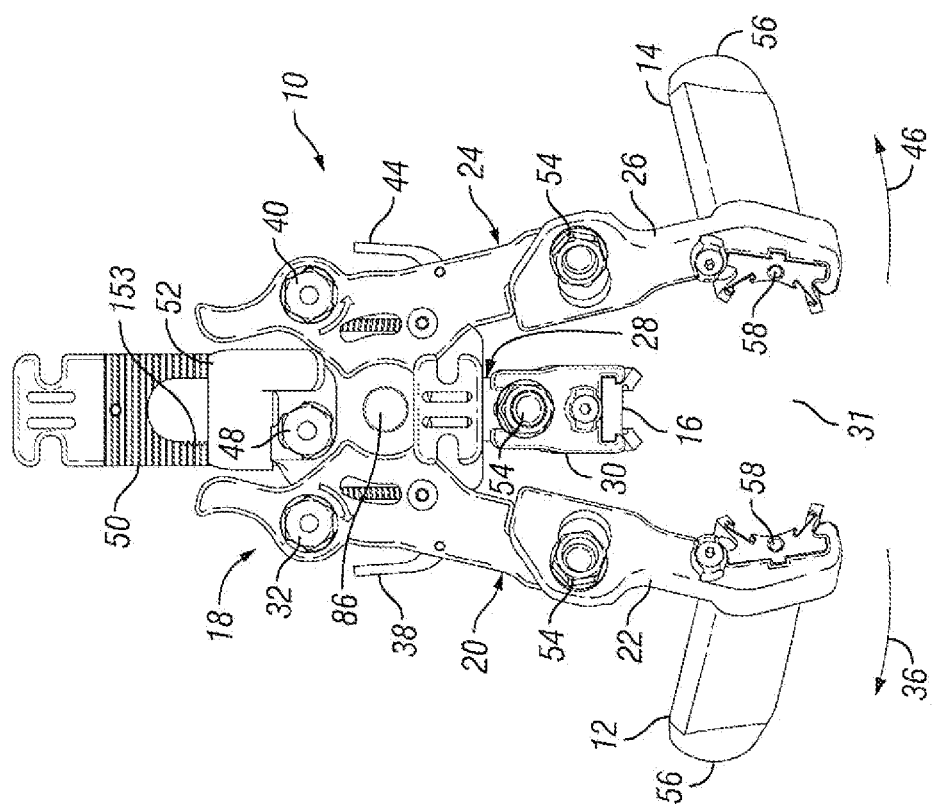

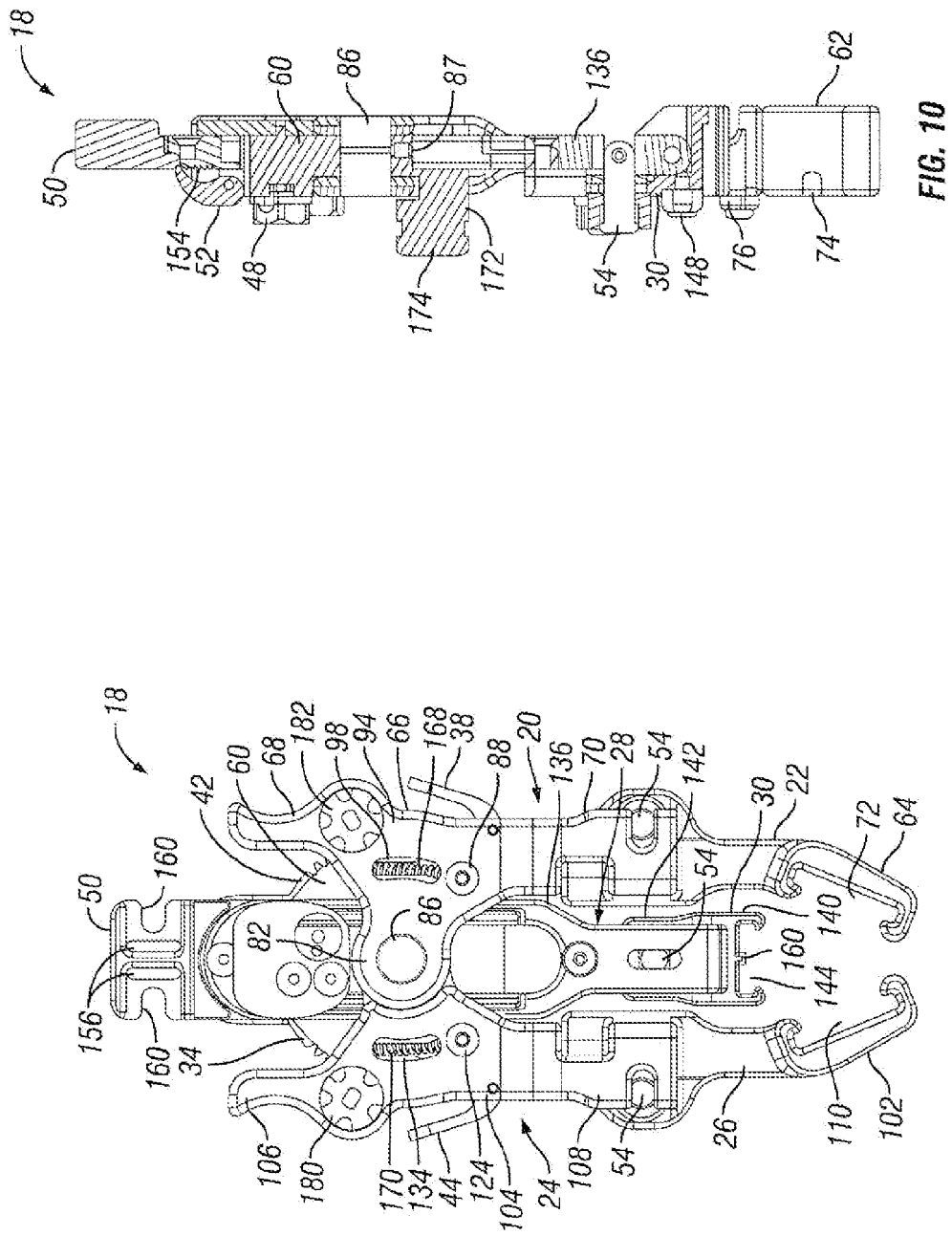

TISSUE RETRACTOR AND METHOD OF USE

FIELD OF THE INVENTION

The present disclosure generally relates to medical devices. In particular, in one or more embodiments, the present disclosure relates to methods and devices for retracting tissue in a surgical procedure to allow access to the surgical site.

BACKGROUND

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray. One typical retractor system may include a plurality of blades coupled to a retractor frame. In use, the blades may be inserted into an incision and then retracted to displace tissue surrounding the incision down to the surgical site. To minimize trauma to the tissue, this tissue displacement should generally be refined and controlled. However, current retractor systems may not provide desired control of the distraction.

Thus, there is a need for improved methods and devices that can be used for retracting tissue to provide access to the surgical site.

SUMMARY

The present disclosure generally relates to medical devices. In particular, in one or more embodiments, the present disclosure relates to methods and devices for retracting tissue in a surgical procedure to allow access to the surgical site.

An embodiment may comprise a retractor system. The retractor system may comprise a retractor frame. The retractor frame may comprise a first rotatable arm, a second rotatable arm, and a linearly translatable arm coupled to the first and second rotatable arms. The first blade may be coupled to a distal end of the first rotatable arm. The first rotatable arm may be configured to rotate to move the first blade in an arc for tissue retraction. The second blade may be coupled to a distal end of the second rotatable arm. The second rotatable arm may be configured to rotate to move the second blade in an arc for tissue retraction. The third blade may be coupled to a distal end of the linearly translatable arm. The linearly translatable arm may be configured to translate to move the third blade in a line for tissue retraction. The first, second, and third blades may be configured to angulate to separate distal ends of the first, second, and third blades from one another for tissue retraction.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

FIGS. 1 and 2 illustrate a retractor system in a closed configuration in accordance with one embodiment of the present technique.

FIGS. 3 and 4 illustrate a retractor system in an open configuration in accordance with one embodiment of the present invention.

FIG. 9 is a bottom view of a retractor frame in accordance with one embodiment of the present invention.

FIG. 10 is a cross-sectional view of a retractor frame in accordance with one embodiment of the present invention.

DETAILED DESCRIPTION OF THE ILLUSTRATED EMBODIMENTS

Figure 5:
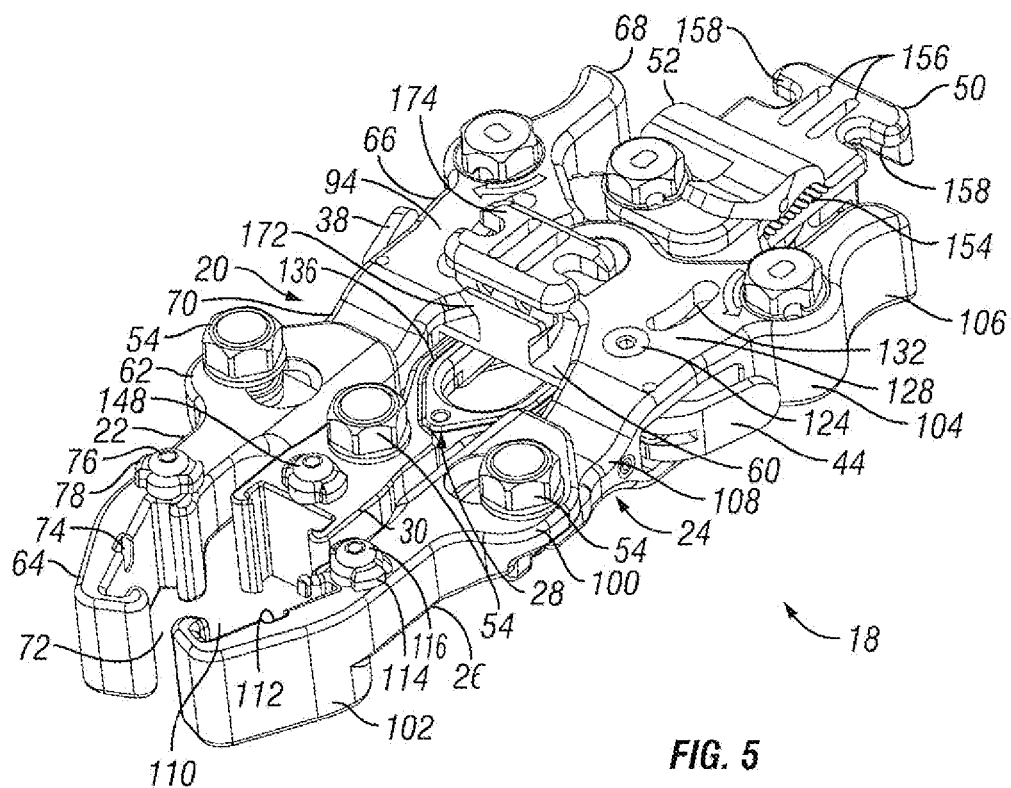
FIG. 5 illustrates a retractor frame in accordance with one embodiment of the present invention.
Figure 6:
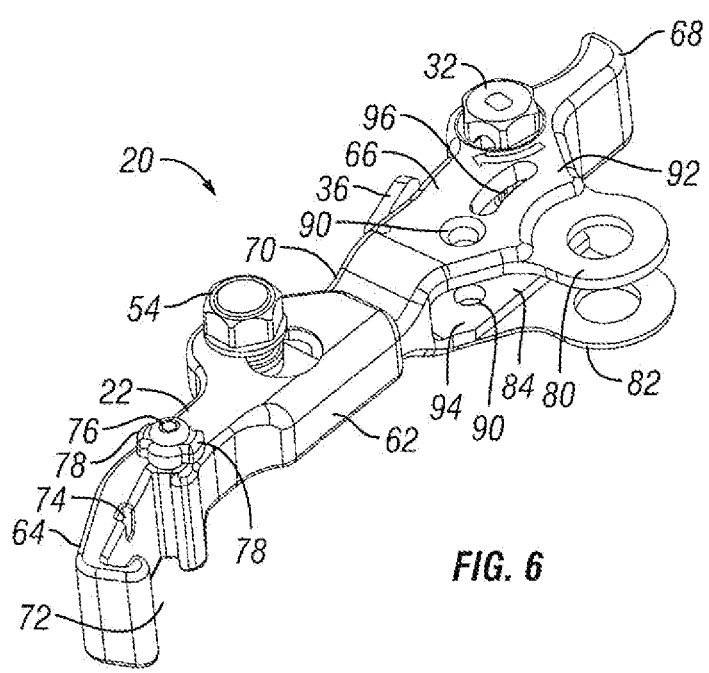
FIG. 6 illustrates a rotatable arm for use in a retractor system in accordance with one embodiment of the present invention.
Figure 7:
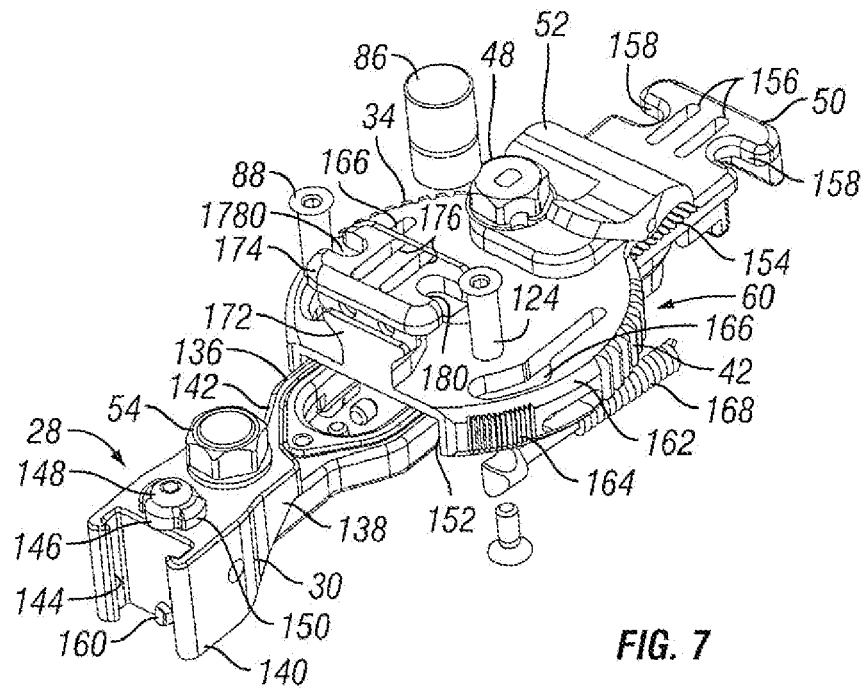
FIG. 7 illustrates a linearly translatable arm and a central gear housing for use in a retractor system in accordance with one embodiment of the present invention.
Figure 8:
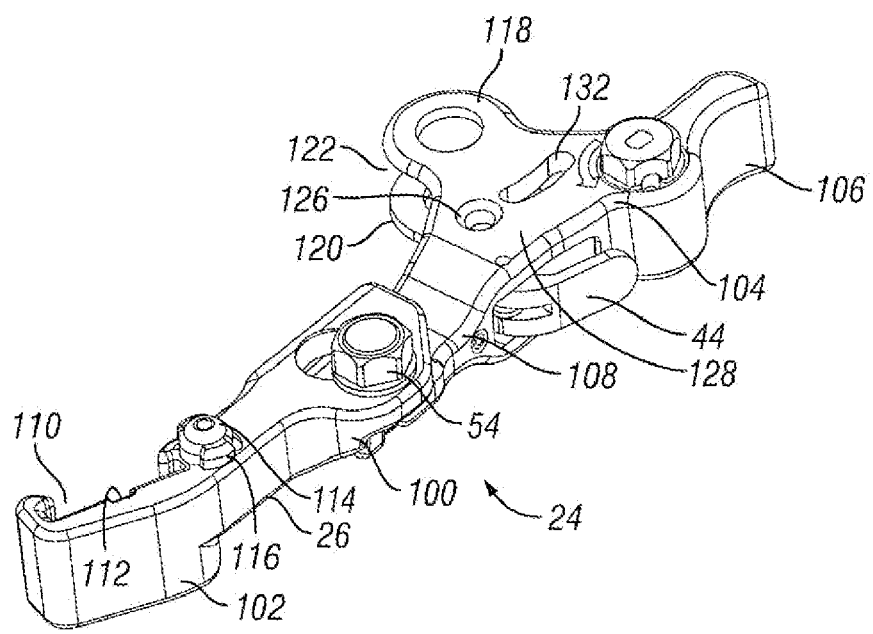
FIG. 8 illustrates a rotatable arm for use in a retractor system in accordance with one embodiment of the present invention.

FIGS. 1-4 illustrate a retractor system 10 that may be used to retract tissue in a surgical procedure in accordance with one embodiment of the present invention. The retractor system 10 comprises a first blade 12, a second blade 14, and a third blade 16. The first, second, and third blades 12, 14, 16 are each coupled to a retractor frame 18. The retractor frame 18 comprises a first rotatable arm 20 having a first blade attachment member 22 for holding and positioning the first blade 12. The retractor frame 18 further comprises a second rotatable arm 24 having a second blade attachment member 26 for holding and positioning the second blade 14. The retractor frame 18 further comprises a linearly translatable arm 28 having a third blade attachment member 30 for holding and positioning the third blade 16. The first and second rotatable arms 20, 24 and the linearly translatable arm 28 may be actuated so that the blades 12, 14, 16 may be separated a desired distance from each other. In addition, the blade attachment members 22, 26, and 30 may be actuated to angulate the blades 12, 14, 16, increasing the distance between the distal ends of the blades 12, 14, 16. In this manner, tissue surrounding an incision may be retracted providing access to the surgical site. In embodiments, the first, second, and third blades 12, 14, 16 may be individually actuated.

FIGS. 1-2 illustrate the retractor system 10 in a "closed" or non-retracted configuration, in accordance with one embodiment of the present invention. In the closed configuration, the first, second, and third blades 12, 14, 16 are radially disposed around a central bore 31 to form a substantially closed, tube-shaped structure.

FIGS. 3-4 illustrate the retractor system 10 in an "open" or retracted configuration, in accordance with one embodiment of the present invention. In the open configuration, the first, second, and third blades 12, 14, 16 have been moved so that they no longer form a tube-shaped structure that is substantially closed. Rather, the first and second blades 12, 14 have been rotated and angulated and third blade 16 has been linearly translated and angulated to enlarge the diameter of the central bore about which the blades 12, 14, 16 are arranged.

The first rotatable arm 20 may be actuated by rotation of an actuator 32. The actuator 32 may be a fastener, such as a hex screw (e.g., a 10 mm hex screw). The actuator 32 may be coupled to a planetary gear 180 (shown on FIG. 9) having teeth that engage a first sun gear 34. The engagement between the actuator 32, the planetary gear 180, and the first sun gear 34 may be described as a planetary gear mechanism in accordance with embodiments of the present invention. In the illustrated embodiments, a ratchet-locking mechanism 38 is included that engages teeth on the first sun gear 34. As the actuator 32 is turned, the first rotatable arm 20 should rotate as indicated by arrow 36 with the distal end of the arm 20 moving in an arc. For example, rotation of the actuator 32 in the counter-clockwise direction drives rotation of the first rotatable arm 20 as indicated by arrow 36 thereby rotating the first blade 12 in an arc away from the second and third blades 14, 16. In an embodiment, the first sun gear 34 is stationary with the planetary gear 180 rotating tooth by tooth along the first sun gear 34. In an embodiment, the ratchet-locking mechanism 38 engages the first sun gear 34 to prevent rotation of the first rotatable arm 20 in the counter-clockwise direction. The first rotatable arm 20 may be released from its rotated state (FIGS. 3-4) by depressing the lever of the ratchet-locking mechanism 38 to allow the first rotatable arm 20 to rotate back to its initial position (FIGS. 1-2).

In a similar manner to the first rotatable arm 20, the second rotatable arm 24 may be actuated by rotation of an actuator 40. The actuator 40 may be, for example, a fastener, such as a hex screw (e.g., a 10 mm hex screw). The actuator 40 may be coupled to a planetary gear 182 (shown on FIG. 9) having teeth that engage a second sun gear 42. The engagement between the actuator 40, the planetary gear 182, and the second sun gear 42 may be described as a planetary gear mechanism in accordance with embodiments of the present invention. It should be understood that use of the term "sun" is not meant to imply that the first and second sun gears 34, 42 are circular in shape but rather that the gears function in conjunction with the other components in a manner similar to what is commonly referred to as a planetary gear. In the illustrated embodiment, a ratchet-locking mechanism 44 is included that engages teeth on the second sun gear 42. As the actuator 40 is turned, the second rotatable arm 24 should rotate as indicated by arrow 46 with the distal end of the second rotatable arm 24 moving in an arc. For example, rotation of the actuator 40 in the counter-clockwise direction should drive rotation of the second rotatable arm 24 as indicated by arrow 46 thereby rotating the second blade 14 in an arc away from the first and third blades 12, 16. In an embodiment, the second sun gear 42 is stationary with the planetary gear 182 rotating tooth by tooth along the second sun gear 42. In an embodiment, the ratchet-locking mechanism 44 engages the second sun gear 42 to prevent rotation of the second rotatable arm 24 in the counter-clockwise direction. The second rotatable arm 24 may be released from its rotated state (FIGS. 3-4) by depressing the lever of the ratchet-locking mechanism 44 to allow the second rotatable arm 24 to rotate back to its initial position (FIGS. 1-2).

The linearly translatable arm 28 may be actuated by rotation of an actuator 48. The actuator 48 may be, for example, a fastener, such as a hex screw (e.g., a 10 mm hex screw). The actuator 48 may be coupled to a pinion gear (not shown) that engages teeth on rack portion 50 of the linearly translatable arm 28. As illustrated, the rack portion 50 may be on the opposite end of the linearly translatable arm 28 from the third blade attachment member 30. The engagement between the actuator 48, the pinion gear, and the rack portion 50 may be described as a rack and pinion gear mechanism in accordance with embodiments of the present invention. In the illustrated embodiment, ratchet-locking mechanism 52 is also included that engages teeth on the rack portion 50. As the actuator 48 is turned, the linearly translatable arm 28 moves in a line as illustrated in FIGS. 3-4. This will increase the distance between the third blade 16 and the first and second blades 12, 14. In an embodiment, the ratchet-locking mechanism 42 engages the rack portion 50 to prevent translation in the opposite direction that would shorten the distance between the blades 12, 14, 16. The linearly translatable arm 28 may be released from its translated state (FIGS. 3-4) by depressing the lever of the ratchet-locking mechanism 52 to allow the linearly translatable arm 28 to rotate back to its initial position (FIGS. 1-2) without having to turn the actuator 48.

In accordance with present embodiments, the first, second, and third blades 12, 14, 16 may be angulated by respective rotation of actuators 54. As used herein, angulation of the blades 12, 14, 16 refers to rotation of the distal ends of the blades 12, 14, 16 outwardly and upwardly, resulting in separation of the distal ends. The actuators 54 may be, for example, a fastener, such as a hex screws (e.g., 10 mm hex screws). As illustrated by FIGS. 3-4, each of the actuators 54 may be rotated to angulate the first, second, and third blades 12, 14, 16, respectively. As will be discussed in more detailed with respect to FIG. 13, rotation of the actuators 54 facilitates this angulation by angulating the blade attachment members 22, 26, 30 to cause corresponding angulation of the blades 12, 14, 16. In an embodiment, the angulation used is an infinite angle adjustment mechanism that is controlled by threading.

The first, second, and third blades 12, 14, 16 of the retractor system 10 may have one or more holes 58 extending through the blades 12, 14, 16 along their respective long axes. The holes 58 may configured to allow passage of light components, k-wires, or other suitable instruments through the blades 12, 14, 16. The edges of the blades may be rounded, for example, to minimize the risk of damage to the retracted tissue. While illustrated with three blades, those of ordinary skill in the art will appreciate the retractor system 10 may include more, or less, than three blades configured to move as desired for a particular application. For example, a retractor system may be used that comprises four blades with two linearly translatable arms and two rotatable arms. Alternatively, a retractor may be used that comprises two rotatable arms or alternatively one linereally translatable arm and one rotatable arm.

It should be understood that the actuators 32, 40, 48, 54 may be configured to engage a variety of different tools to facilitate the desired rotation. For example, wrenches, screwdrivers, or any other suitable tools may be used to rotate the actuators 32, 40, 48, 54. In addition, while actuators 32, 40, 48, 54 are shown as fasteners, it should be understood that fasteners are not required to facilitate the movement. Other suitable devices, such as cranks, may be used to facilitate the desired movement.

An embodiment of the present invention includes using the retractor system 10 to retract tissue in a surgical procedure. For example, the retractor system 10 may be placed into an opening (e.g., an incision) in the patient's tissue with the retractor system 10 in the closed position. The surgeon (or other operator) may then separately rotate actuator 32 and actuator 40 to rotate the first rotatable arm 20 and the second rotatable arm 24, respectively, thus moving the first and second blades 12, 14 in an arc. The surgeon may also rotate actuator 48 to move the linearly translatable arm 28 and, thus, the third blade 16, in a line. In this manner, the first, second, and third blades 12, 14, 16 may be retracted (or spread) to provide enhanced access to the surgical site. To further enhance access, the surgeon may rotate each of actuators 54 to angulate the first, second, and third blades 12, 14, 16.

Turning now to FIGS. 5-11, the retractor frame 18 is illustrated in more detail in accordance with embodiments of the present invention. As previously mentioned, the retractor frame 18 may comprise a first rotatable arm 20, a second rotatable arm 24, and a linearly translatable arm 28. A portion of the second rotatable arm 24 is removed on FIG. 11 to illustrate interior components of the retractor frame 18. In addition, the retractor frame 18 may further comprise a central gear housing 60. As illustrated, the central gear housing 60 houses the first sun gear 34 and the second sun gear 42. In accordance with present embodiments, the first sun gear 34 and the second sun gear 42 are configured to facilitate rotation of the first rotatable arm 20 and the second rotatable arm 24, respectively.

The first rotatable arm 20 may comprise a first blade attachment member 22 having a proximal end 62 and a distal end 64. The first rotatable arm 20 may further comprise a base portion 66 having a proximal end 68 and a distal end 70. The proximal end 62 of the first blade attachment member 22 may be disposed over the distal end 70 of the base portion 66. The first blade attachment member 22 may be secured to the base portion 66 by a pivot pin (not shown). The distal end 64 of the first blade attachment member 22 may be configured to receive the first blade 12 (illustrated on FIGS. 1 and 3). For example, the distal end 64 may have a slot 72 that receives the first blade 12. A notch 74 in the distal end 64 may receive a corresponding protrusion in the first blade 12. Fastener 76 may secure the first blade 12 in the blade attachment member 22. As illustrated, the fastener 76 may include one or more radially extending protrusions 78. To secure the first blade 12, the first blade 12 may be inserted into slot 72 until the protruding portion of the blade 12 lands on the notch 74. The fastener 76 may be rotated until one of the protrusions 78 extends over the top of the first blade 12 to prevent its removal from the slot 72.

The base portion 66 may have a finger grip at the proximal end 68 that may be used to facilitate a controlled return of the first rotatable arm 20 after depression of the ratchet-locking mechanism 38. Top and bottom annular-shaped members 80, 82 may extend laterally from the first rotatable arm 22. Slot 84 may be formed in the first rotatable arm 20 for receiving the central gear housing 60. Pin 86 may extend through the annular-shaped members 80, 82 to secure the central gear housing 60 in the slot 84 with the teeth of the first sun gear 34 engaging the planetary gear 180. Set screw 87 should secure the pin 88 in the central gear housing 60. Pin 88 may extend through holes 90 in the upper and lower portions 92, 94 of the base portion 66. Pin 88 should be coupled to spring 170 for spring-loading the first rotatable arm 20. Upper slot 96 may be formed in the upper portion 92 of the base portion 66 to provide access to the central gear housing 60 and other components of the retractor frame 18. As illustrated by FIG. 9, there may be a corresponding lower slot 98 formed in the lower portion 94 of the base portion 66 that can provide access to the central gear housing 60 and other components of the retractor frame 18.

The second rotatable arm 24 may comprise a second blade attachment member 26 having a proximal end 100 and a distal end 102. The second rotatable arm 24 may further comprise a base portion 104 having a proximal end 106 and a distal end 108. The proximal end 100 of the second blade attachment member 26 may be disposed over the distal end 108 of the base portion 104. The second blade attachment member 26 may be secured to the base portion 104 by a pivot pin 105 (shown on FIG. 12). The distal end 102 of the second blade attachment member 26 may be configured to receive the second blade 14 (illustrated on FIGS. 1 and 3). For example, the distal end 102 may have a slot 110 that receives the second blade 14. A notch 112 in the distal end 102 may receive a corresponding protrusion in the second blade 14. Fastener 114 may secure the second blade 14 in the second attachment member 26. As illustrated, the fastener 114 may include one or more radially extending protrusions 116. To secure the second blade 14, it may be inserted into slot 110 until the protruding portion of the blade 14 lands on the notch 112. The fastener 114 may then be rotated until one of the protrusions 116 extends over the top of the second blade 14 to prevent its removal from the slot 110.

The base portion 104 may have a finger grip at the proximal end 106 that may be used to facilitate a controlled return of the second rotatable arm 24 after depression of the ratchet-locking mechanism 38. Top and bottom annular-shaped members 118, 120 may extend laterally from the second rotatable arm 26. Slot 122 may be formed in the second rotatable arm 24 for receiving the central gear housing 60. Pin 86 may extend through the annular-shaped members 118, 120 to secure the central gear housing 60 in the slot 122 with the teeth of the second sun gear 42 engaging the planetary gear 182. Pin 124 may extend through holes 126 in the upper and lower portions 128, 130 of the base portion 104. Pin 124 should be coupled to spring 168 for spring-loading the second rotatable arm 24. Upper slot 132 may be formed in the upper portion 128 of the base portion 104 to provide access to the central gear housing 60 and other components of the retractor frame 18. As illustrated by FIG. 9, there is a corresponding lower slot 134 formed in the lower portion 130 of the base portion 104 that can provide access to the central gear housing 60 and other components of the retractor frame 18.

The linearly translatable arm 28 may comprise a third blade attachment member 30 and a rack portion 50 separated from third blade attachment member 30 by a slotted middle portion 136. In an embodiment, the rack portion 50 may be at least partially slotted. The third blade attachment member 30 may have a proximal end 138 and distal end 140. The slotted middle portion 136 may comprise a distal end 142 on which the proximal end 138 of the third blade attachment member 30 may be disposed. A pin may secure the third blade attachment member 30 to the slotted middle portion 136. The distal end 140 of the third blade attachment member 30 may be configured to receive the third blade 16 (illustrated on FIGS. 1 and 3). For example, the distal end 140 may have a slot 144 that receives the third blade 16. A notch 146 in the distal end 140 may receive a corresponding protrusion in the third blade 16. Fastener 148 may secure the third blade 16 in the third blade attachment member 30. As illustrated, the fastener 148 may include one or more radially extending protrusions 150. To secure the third blade 16, it may be inserted into slot 144 until the protruding portion of the blade 16 lands on the notch 146. The fastener 148 may then be rotated until one of the protrusions 150 extends over the top of the third blade 16 to prevent its removal from the slot 144. A protrusion 160 in the bottom of the slot 144 may further secure the third blade 16 in the slot 144.

The slotted middle portion 136 may be coupled to the third blade attachment member 30 at its distal end 142 with the rack portion 50 on its other end. As illustrated, the slotted middle portion 136 may extend into a through passageway 152 in the central gear housing 60. The slotted middle portion 136 separates the rack portion 50 from the third blade attachment member 30. As illustrated, the rack portion 50 may extend from the through passageway 152 in the central gear housing 60. The rack portion 50 may further comprise rack teeth 153 that should engage with the actuator/pinion gear 48. Ratchet-locking mechanism 52 may further engage teeth 154 on the rack portion 50. The rack portion 50 may further comprise features for securing the retractor system 10 to an arm (not illustrated). Those of ordinary skill in the art should understand that the arm may be used to provide, for example, a connection between the retractor system 10 and an operating table. The features for securing the retractor system 10 to the arm may include, for example, a pair of slots 156 and semi-elliptical openings 158 on opposing sides of the rack portion 50.

The central gear housing 60 may comprise a first sun gear 34 on a first side and a second sun gear 42 on a second side. In the illustrated embodiment, the central gear housing 60 is generally disc shaped with a rim 162 about which the first sun gear 34 and the second sun gear 42 are individually rotatable. As illustrated, the rim 162 may further comprise teeth 164 that engage the ratchet-locking mechanism 44 of the second rotatable arm 24. While not illustrated, there may be corresponding teeth on the opposite side of the rim 162 for engaging the ratchet-locking mechanism 38 for the first rotatable arm 20. A central opening may be disposed in the central gear housing 60 through which pin 86 may be inserted. Central gear housing 60 may further comprise a through passageway 152 having a rectangular cross section. Central gear housing 60 may further comprise channels 166. In the illustrated embodiment, spring 170 may be coupled to pin 88 for providing the force to return the first rotatable arm 20 to its initial position when the ratchet-locking mechanism 38 is released. As further illustrated, pin 124 may be inserted into the other one of the channels 166. Spring 168 may be coupled to pin 124 for providing force to return the second rotatable arm 24 to its initial position when the ratchet-locking mechanism 44 is released. Central gear housing 60 may further comprise upwardly extending arm 172 to which arm attachment plate 174 may be attached. Arm attachment plate 174 may comprise features for attaching the retractor system 10 to a table connector, such as an arm. For example, arm attachment plate 174 may comprise slots 176 and semi-elliptical openings 178. As illustrated, ratchet-locking mechanism 52 may be coupled to the central gear housing 60 so as to engage teeth 154 on the rack portion 50 of the linearly translatable arm 28. As further illustrated, actuator 48 may extend through an opening in the central gear housing 60 so that a connected pinion gear (not illustrated) also engages the rack teeth 153.

Figure 12:
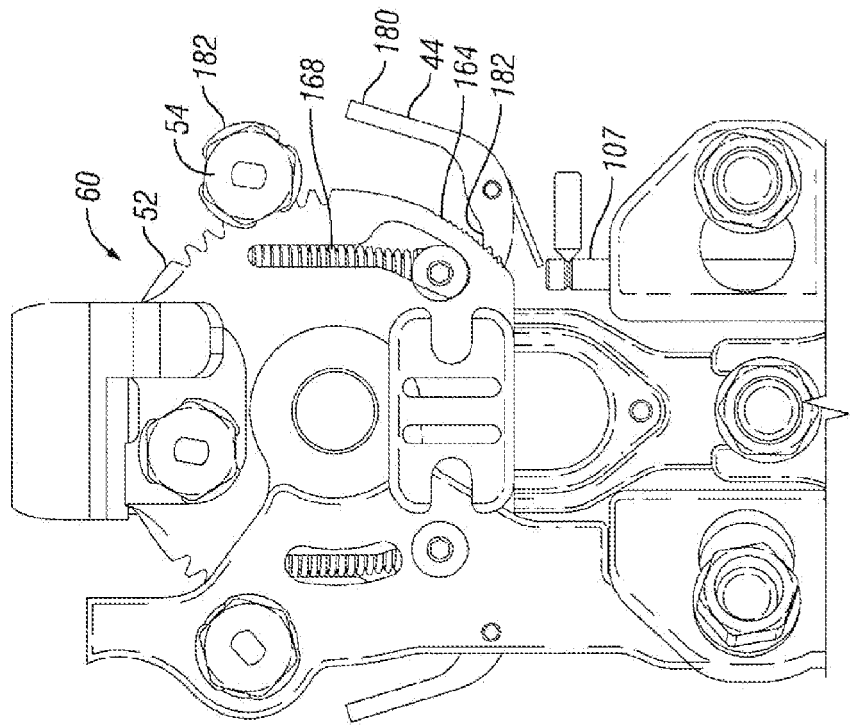
FIG. 12 illustrates a ratchet-locking mechanism in accordance with one embodiment of the present invention.
Figure 11:
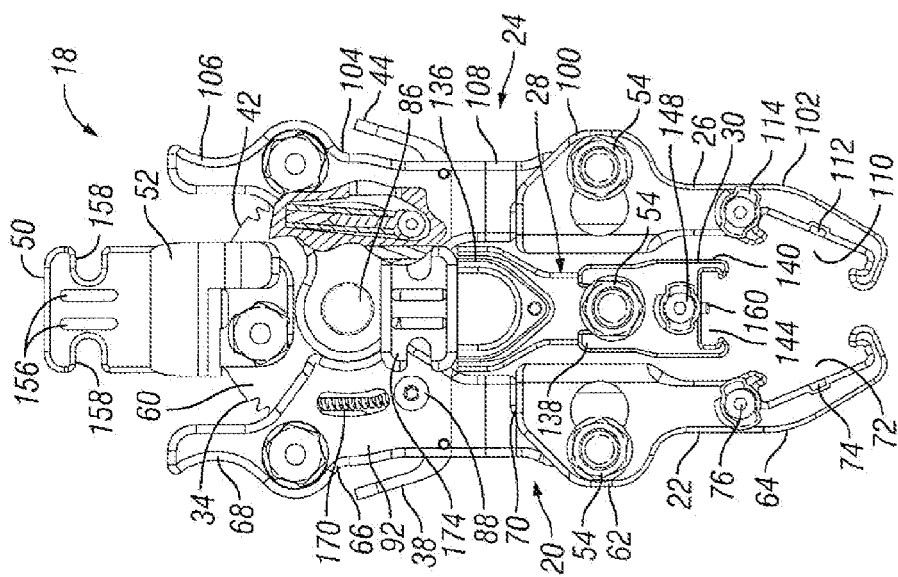
FIG. 11 is a top view of a retractor frame in accordance with one embodiment of the present invention.

FIG. 12 illustrates the ratchet-locking mechanism 44 in more detail in accordance with one embodiment of the present invention. In an embodiment, the ratchet-locking mechanism 44 includes a lever 180 and a nose 182. As illustrated, the nose 182 of the ratchet-locking mechanism 44 engages teeth 164 on the central gear housing 60. As previously discussed, rotation of the actuator 54 in the counter-clockwise direction should drive the planetary gear 182 tooth by tooth along the second sun gear 52. Rotation of the actuator 54 should drive corresponding rotation of the second rotatable arm 24 in the counter-clockwise direction. The nose 182 of the ratchet-locking mechanism 44 should engage the teeth 164 of the second sun gear 52 to allow movement of the second rotatable arm 24 in one direction, i.e., the counter-clockwise direction. The second rotatable arm 24 can be released from this rotated position by depressing the lever 180. The spring 168 should generally provide the force need to return the second rotatable arm 24 to its initial position when the lever 180 is released. While the previous discussion of FIG. 12 is with respect to the ratchet-locking mechanism 44, it should be understood that ratchet-locking mechanism 38 may be operated in a similar manner to restrict rotation of the first rotatable arm 20. It should further be noted that, while the previous discussion describes a ratchet-locking mechanism, other suitable devices for allowing movement of the rotatable arms in one direction may be used in accordance with the present invention.

Figure 13:
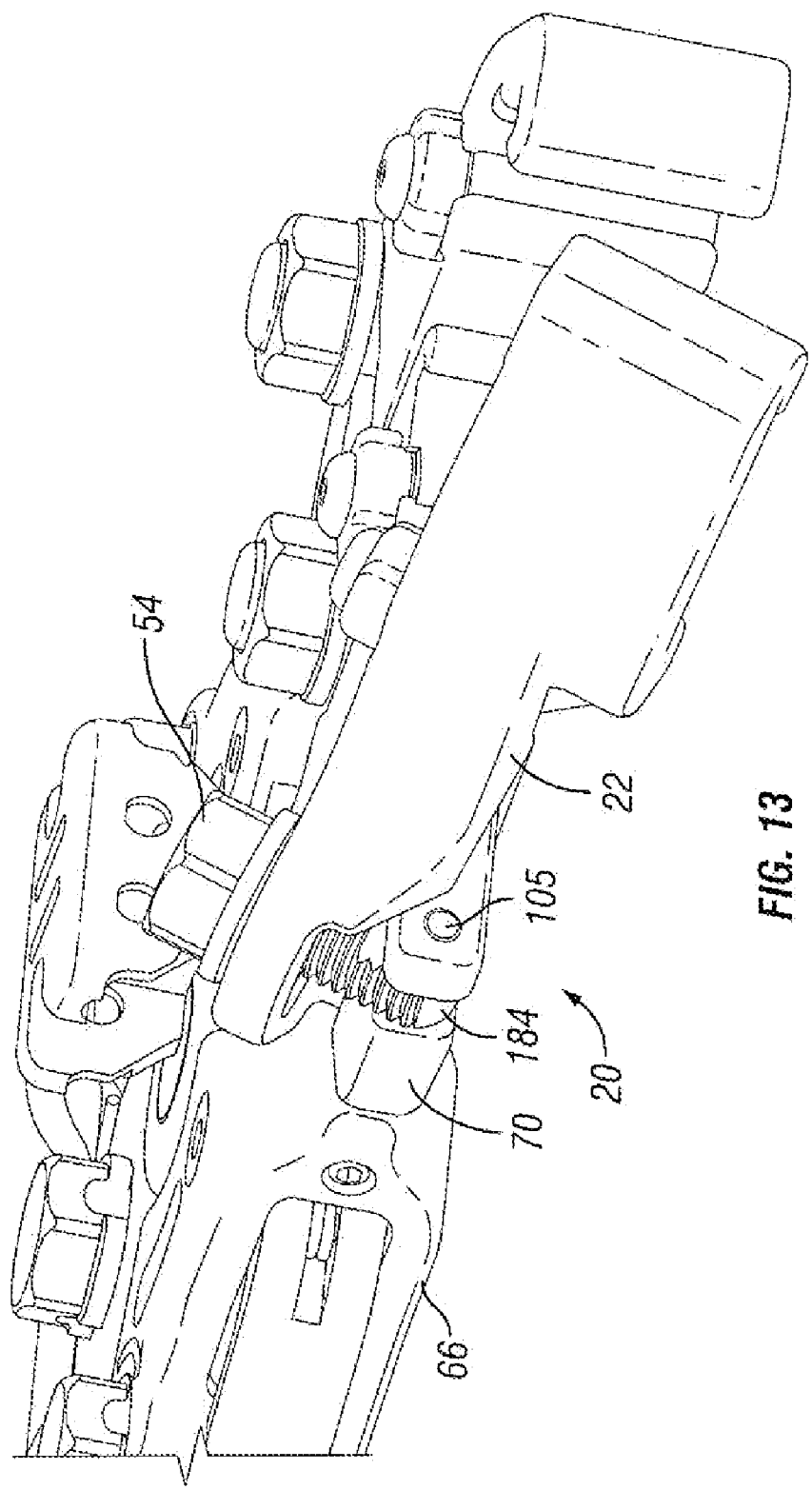
FIG. 13 illustrates angulation of a retractor blade in accordance with one embodiment of the present invention.

FIG. 13 describes angulation of the blade attachment member 22 in accordance with one embodiment of the present invention. As previously discussed, the first rotatable arm 20 comprises blade attachment member 22 coupled to the distal end 70 of the base portion 66. As illustrated, actuator 54 may secure the blade attachment member 22 onto the base portion 66. The actuator 54 may be threaded, for example, into a corresponding opening 184 in the base portion 66. The pin 107 (See FIG. 12) pivotably connects the attachment member 22 to the screw shaft of the actuator 54. A second pin 105 (See FIG. 13) connects the attachment member 22 through the base portion of the 66. The screw head of the actuator is provided with a portion that allows the attachment member to be retained within the head portion of the actuator and is pivotably rotatable when the actuator 54 is manipulated. The pin 107 and pin 105 create two separate axis of rotations. As the actuator is manipulated the attachment member 22 is rotated along the axis of rotation of pin 105. In an embodiment, the opening 184 may be angled, in that the axis of the opening 184 may be at an angle with respect to the z-axis of the first rotatable arm 20. Accordingly, as the actuator 54 is rotated, the blade attachment member 22 should pivot. In this manner, the blade attachment member 22 and, thus, the first blade 12 may be angulated. While the previous discussion of FIG. 12 and FIG. 13 is with respect to angulation of the first blade attachment member 22, it should be understood that second and third blade attachment members 26, 30 may be angulated in a similar manner. It should further be noted that, while the previous discussion describes an angled actuator for angulating the blade attachment member 22, 26, and 30, other suitable mechanisms for facilitating the desired blade angulation may be used in accordance with the present invention.

While it is apparent that the invention disclosed herein is well calculated to fulfill the objects stated above, it will be appreciated that numerous modifications and embodiments may be devised by those skilled in the art.

What is claimed is:

1. A retractor system comprising:
   a retractor frame comprising a first rotatable arm, a second rotatable arm, and a linearly translatable arm coupled to the first and second rotatable arms;
   a first blade coupled to a distal end of the first rotatable arm, wherein the first rotatable arm is configured to rotate to move the first blade in an arc for tissue retraction;
   a second blade coupled to a distal end of the second rotatable arm, wherein the second rotatable arm is configured to rotate to move the second blade in an arc for tissue retraction;
   a third blade coupled to a distal end of the linearly translatable arm, wherein the linearly translatable arm is configured to translate to move the third blade in a line for tissue retraction,
   wherein the first, second, and third blades are configured to angulate to separate distal ends of the first, second, and third blades from one another for tissue retraction,
   wherein rotation of the first arm and second arm is performed independently from angulation of the first blade and second blade and wherein rotation of the first arm and second arm is in a different direction from angulation of the first blade and second blade.

2. The retractor system of claim 1 wherein the first rotatable arm and the second rotatable arm are independently rotatable.

3. The retractor system of claim 1 wherein the distal end of the first rotatable arm comprises a blade attachment member for holding the first blade, wherein the blade attachment member is configured to actuate to move a distal end of the first blade away from distal ends of the second and third blades.

4. The retractor system of claim 1 wherein the retractor frame comprises a planetary gear mechanism for driving rotation of the first rotatable arm.

5. The retractor system of claim 1 wherein the retractor frame comprises an actuator coupled to the first rotatable arm, wherein rotation of the actuator is configured to actuate rotation of the first rotatable arm.

6. The retractor system of claim 5 wherein the retractor frame comprises a planetary gear coupled to the actuator such that rotation of the actuator rotates the planetary gear, and wherein the retractor system comprises a sun gear that engages the planetary gear.

7. The retractor system of claim 1 wherein the retractor frame comprises a ratchet-locking mechanism for locking rotation of the first rotatable arm.

8. The retractor system of claim 1 wherein the retractor frame comprises a rack and pinion gear mechanism for translation of the linearly translatable arm.

9. The retractor system of claim 1 wherein the linearly translatable arm comprises a rack portion for facilitating translation of the linearly translatable arm.

10. The retractor system of claim 1 wherein the retractor frame comprises a ratchet-locking mechanism for locking translation of the linearly translatable arm.

11. A retractor system comprising:
a retractor frame comprising:
a first rotatable arm comprising a first blade attachment member at a distal end of the first rotatable arm;
a first planetary gear mechanism coupled to the first rotatable arm for rotating the first rotatable arm to move the distal end of the first rotatable arm in an arc;
a second rotatable arm comprising a second blade attachment member at a distal end of the second rotatable arm;
a second planetary gear mechanism coupled to the second rotatable arm for rotating the second rotatable arm to move the distal end of the second rotatable arm in an arc;
a linearly translatable arm coupled to the first rotatable arm and the second rotatable arm, the linearly translatable arm comprising a third blade attachment member at a distal end of the linearly translatable arm; and
a rack and pinion gear mechanism for translating the linearly translatable arm in a line;
a first blade coupled to the first blade attachment member;
a second blade coupled to the second blade attachment member; and
a third blade coupled to the third blade attachment member, wherein the first, second, and third blades are configured to angulate to separate distal ends of the first, second, and third blades from one another
wherein rotation of the first rotatable arm and second rotable arm is performed independently from angulation of the first blade and second blade and wherein rotation of the first rotatable arm and second rotatable arm is in a different direction from angulation of the first blade and second blade.

12. The retractor system of claim 11 wherein the first rotatable arm comprises a base portion having a distal end coupled to a proximal end first blade attachment member.

13. The retractor system of claim 12 wherein the first planetary gear mechanism comprises an actuator, a planetary gear coupled to the actuator such that rotation of the actuator rotates the planetary gear, and a first sun gear coupled to the first rotatable arm and engaging teeth on the planetary gear.

14. The retractor system of claim 13 wherein the first sun gear is received within a slot in the base portion of the first rotatable arm.

15. The retractor system of claim 14 wherein the retractor frame comprises a central gear housing coupled to the first rotatable arm, the second rotatable arm, and the linearly translatable arm, wherein the central gear housing houses the first sun gear.

16. The retractor system of claim 11 wherein the retractor frame comprises a ratchet-locking mechanism for locking rotation of the first rotatable arm.

17. The retractor system of claim 11 wherein the linearly translatable arm comprises a rack portion and a slotted portion, wherein the slotted portion separates the rack portion from the third blade attachment member.

18. The retractor system of claim 11 wherein the rack and pinion gear mechanism comprises an actuator, wherein rotation of the actuator results in translation of the linearly translatable arm in a line.

19. The retractor system of claim 11 wherein the retractor frame comprises a ratchet-locking mechanism for locking translation of the linearly translatable arm.

20. A method for retracting tissue in a surgical procedure comprising:
providing a retractor system comprising:
a retractor frame comprising a first rotatable arm, a second rotatable arm; and
a linearly translatable arm coupled to the first and second rotatable arms;
a first blade coupled to a distal end of the first rotatable arm;
a second blade coupled to a distal end of the second rotatable arm; and
a third blade coupled to a distal end of the linearly translatable arm;
rotating the first arm so that the first blade moves in an arc to retract tissue;
rotating the second arm so that the second blade moves in an arc to retract tissue;
translating the third arm so that the third blade moves in a line to retract tissue; and
angulating the first, second, and third blades to move distal ends of the first, second, and third blades away from one another to retract tissue
wherein rotation of the first arm and second arm is performed independently from angulation of the first blade and second blade and wherein rotation of the first arm and second arm is in a different direction from angulation of the first blade and second blade.

* * * * *